(12) United States Patent
Dive et al.

(10) Patent No.: US 6,630,501 B1
(45) Date of Patent: Oct. 7, 2003

(54) PHOSPHINIC PSEUDO-PEPTIDES THAT MAY BE USED AS MATRIX ZINC METALLOPROTEASE INHIBITORS

(75) Inventors: Vincent Dive, Palaiseau (FR); Philippe Cuniasse, Paris (FR); Marie-Christine Rio, Illkirch (FR); Paul Basset, deceased, late of Strasbourg (FR), by Genevieve Basset, legal representative; Athanasios Yotakis, Paraskevi (GR); Fabrice Beau, Massy (FR); Stamania Vassiliou, Kareas-Athenes (GR)

(73) Assignees: Commissariat a l'energie Atomique, Paris; Institut National de la Recherche Medical, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/869,303

(22) PCT Filed: Jan. 18, 2000

(86) PCT No.: PCT/FR00/00093

§ 371 (c)(1),
(2), (4) Date: Mar. 25, 2002

(87) PCT Pub. No.: WO00/43404

PCT Pub. Date: Jul. 27, 2000

(30) Foreign Application Priority Data

Jan. 19, 1999 (FR) .............................. 99 00509

(51) Int. Cl.$^7$ .................... A61K 31/404; C07D 209/04; C07F 9/572

(52) U.S. Cl. ...................... 514/419; 548/414; 548/491; 564/15; 514/7

(58) Field of Search ................. 548/414, 491; 514/419, 7; 564/15

(56) References Cited

U.S. PATENT DOCUMENTS

| | | |
|---|---|---|
| 5,500,414 A | 3/1996 | Dive et al. |
| 5,677,281 A | 10/1997 | Dive et al. |
| 5,776,903 A | 7/1998 | Dive et al. |

FOREIGN PATENT DOCUMENTS

| | | |
|---|---|---|
| EP | 0 725 075 | 8/1996 |
| FR | 2 676 059 | 11/1992 |
| FR | 2 689 764 | 10/1993 |
| WO | WO 93/14112 | 7/1993 |
| WO | WO 98/03516 | 1/1998 |

OTHER PUBLICATIONS

Basset et al (2000): STN International, CAPLUS database, (Columbus, Ohio)No. 133: 120685.*
Vassiliou et al (1999):STN International, CAPLUS database, (Columbus, Ohio)No. 131: 157958.*

A. Mucha, et al., *The Journal of Biological Chemistry*, vol. 273, No. 5, pp. 2763–2768, (1998).*
J. L. Goulet, et al., Bioorganic & Medicinal Chemistry Letters, vol. 4, No. 10, pp. 1221–1224, "Inhibition of Stromelysin–1 (MMP–3) by Peptidyl Phosphinic Acids", 1994.
S. Vassiliou, et al., Journal of Medicinal Chemistry, vol. 42, No. 14, pp. 2610–2620, "Phosphinic Pseudo–Tripeptides as Potent Inhibitors of Matrix Metalloproteinases: A Structure–Activity Study", Jul. 15, 1999.
J. E. Baldwin, et al., J. Chem. Soc., Chem. Commun., pp. 1339–1340, "Radical Reactions in Synthesis: Carbon–Carbon Bond Formation From 2–Substituted Allyl Trialkyl Stannanes", 1986.
E. Keith Baylis, et al., J. Chem. Soc. Perkin Trans. I, pp. 2845–2853, "1–Aminoalkylphosphonous Acids. Part 1. Isosteres of the Protein Amino Acids", 1984.
R. P. Beckett, et al., Exp. Opin. Ther. Patents, vol. 8, No. 3, pp. 259–281, "Matrix Metalloproteinase Inhibitors 1998", 1998.
P.D. Brown, Medical Oncology, vol. 14, No. 1, pp. 1–10, "Matrix Metalloproteinase Inhibitors in the Treatment of Cancer", 1997.

(List continued on next page.)

Primary Examiner—Joseph K. McKane
Assistant Examiner—Golam M. M. Shameem
(74) Attorney, Agent, or Firm—Oblon, Spivak, McClelland, Maier & Neustadt, P.C.

(57) ABSTRACT

The invention relates to pseudo-peptides according to the formula:

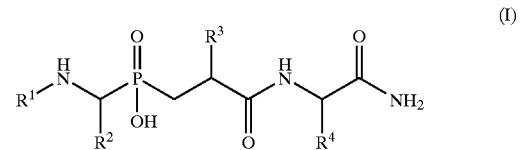

(I)

wherein
$R^1$ is a group inhibiting an amine function, or an amino acid residue or peptide with an inhibited terminal amino function,
$R^2$ represents the lateral chain of a natural or non-natural amino acid,
$R^3$ represents:
1) the lateral chain of a natural amino acid except for Gly and Ala, not substituted or substituted by an aryl group,
2) an aralkyl group, or
3) an alkyl group comprising at least 3 carbon atoms, and
$R^4$ represents a lateral chain of natural or non-natural amino acid.

They are useful as matrix zinc metalloprotease inhibitors, particularly in the treatment of cancer.

22 Claims, 2 Drawing Sheets

OTHER PUBLICATIONS

C. G. Caldwell, et al., Bioorganic & Medicinal Chemistry Letters, vol. 6, No. 3, pp. 323–328, "Phosphinic Acid Inhibitors of Matrix Metalloproteinases", 1996.

T. H. Corbett, et al., Cancer Research, vol. 35, pp. 2434–2439, "Tumor Induction Relationships in Development of Transplantable Cancers of the Colon in Mice for Chemotherapy Assays, with a Note on Carcinogen Structure", Sep. 1975.

K. Eistetter, et al., Journal of Medicinal Chemistry, vol. 25, No. 2, pp. 109–113, "Synthesis and Hypoglycemic Activity of Phenylalkyloxiranecarboxylic Acid Derivatives", 1982.

A. Horovits, et al., Proc. Natl. Acad. Sci. USA, vol. 84, pp. 6654–6658, "An Accurate Method for Determination of Receptor–Ligand and Enzyme–Inhibitor Dissociation Constants From Displacement Curves", Oct. 1987.

J. Jiracek, et al., The Journal of Biological Chemistry, vol. 271, No. 32, pp. 19606–19611, "Development of The First Potent and Selective Inhibitor of the Zinc Endopeptidase Neurolysin Using a Systematic Approach Based on Combinatorial Chemistry of Phosphinic Peptides", Aug. 9, 1996.

J. Jiracek, et al., The Journal of Biological Chemistry, vol. 270, No. 37, pp. 21701–21706, "Development of Highly Potent and Selective Phosphinic Peptide Inhibitors of Zinc Endopeptidase 24–15 Using Combinatorial Chemistry", Sep. 15, 1995.

A. Yiotakis, et al., The Journal of Organic Chemistry, vol. 61, No. 19, pp. 6601–6605, "Protection of the Hydroxyphosphinyl Function of Phosphinic Dipeptides by Adamantyl. Application to the Solid–Phase Synthesis of Phosphinic Peptides", 1996.

* cited by examiner

PHOSPHINIC PSEUDO-PEPTIDES THAT MAY BE USED AS MATRIX ZINC METALLOPROTEASE INHIBITORS

This application is a 371 of PCT/FR00/00093 Jan. 18, 2000.

FIELD OF THE INVENTION

The present invention relates to phosphinic pseudo-peptides that may particularly be used as very powerful and specific inhibitors for matrix zinc metalloproteases MMP, particularly MMP-11, MMP-2, MMP-9 and MMP-8. However, these pseudo-peptides appear to show a low activity with respect to MMP-1 and MMP-7. In this way, these inhibitors offer the possibility to only inhibit one MMP sub-family in vivo, and could therefore prove to be less toxic than MMP inhibitors with a very broad spectrum of activity.

Said pseudo-peptides may have applications in the treatment of diseases characterised by the over-expression of matrix proteases, such as connective and joint tissue degeneration, rheumatoid arthritis, osteoarthritis, aortic aneurysm and cancer.

On the basis of the studies conducted in vivo on animals, these phosphinic inhibitors appear to allow use in pharmaceutical formulations to inhibit primary or secondary tumour growth.

STATE OF THE RELATED ART

Matrix zinc metalloproteases MMP represent a family of enzymes collectively capable of splitting all the proteins of the extracellular matrix. Due to their role on extracellular matrix proteins, these enzymes play a very important role during the development and the course of various tissue remodelling processes, such as involution of the mammary gland, cicatrisation and extravasion of specialised immune response cells.

Around fifteen enzymes in humans belonging to the MMP family are known to date:

| Matrixins | |
|---|---|
| MMP-1 | Interstitial collagenase |
| MMP-8 | Neutrophil collagenase |
| MMP-13 | Collagenase 3 |
| MMP-18 | Collagenase 4 |
| MMP-3 | Stromelysin 1 |
| MMP-10 | Stromelysin-2 |
| MMP-11 | Stromelysin-3 |
| MMP-2 | Gelatinase-A |
| MMP-9 | Gelatinase-B |
| MMP-12 | Metalloelastase |
| MMP-14 | MT-1 MMP |
| MMP-15 | MT-2 MMP |
| MMP-16 | MT-3 MMP |
| MMP-17 | MT-4 MMP |
| MMP-7 | Matrilysin |

Collagenases appear to be the only MMPs to be capable of splitting collagen in fibrillary form. Gelatinases A and B are characterised by their ability to split type IV collagen, which is very abundant in the basal membranes and collagen in denatured form. Stromelysins 1 and 2 appear to be responsible for the breakdown of other proteins of the extracellular matrix, such as fibronectin and various proteoglycans. MT-MMPs appear to be above all involved in the activation of gelatinase A, and due to their membrane location, these matrixins appear to play a role as a membrane receptor of gelatinase A. It is important to note that the physiological substrate of stromelysin-3 is not known to date. However, several studies on this protease, which was initially characterised in breast tumours, suggest that stromelysin-3 is an important factor in the development and survival of tumours.

MMPs appear to be over-expressed in various human diseases, particularly cancer. In this disease, for a long time, the role of MMPs was associated with the invasion of tumour cells and their ability to pass through various barriers to form secondary tumours. More recently, various studies have established that said proteases certainly play a more fundamental role in carcinogenesis, particularly by taking part in primary tumour growth. Of different theories to explain this function of MMPs, the most studied relate to their role in:

their ability, by means of extracellular matrix protein proteolysis, to release from said matrix the growth factors essential for the development and survival of tumours, and angiogenesis, required for tumour growth.

The apparent involvement of MMPs in tumour growth has led numerous teams world-wide to focus on the role of compounds capable of inhibiting these enzymes.

Synthesis programmes on MMP inhibitors were initiated a number of years ago. At this time, applications of MMP inhibitors particularly related to inflammatory diseases of the connective tissue. It was only more recently that multiple programmes on the application of MMP inhibitors in cancerology have developed, as described by Brown, Medical Oncology, 1997, 14, 1–10, [1]. Indeed, as mentioned above, the studies demonstrating that MMPs must be considered as priority targets in the development of new anticancer agents are relatively recent. As such, it may be noted that, in 1997, 67 patents relating to MMP inhibitors were registered worldwide, the majority of which relate to cancerology applications, as described by Beckett et al, 1998, Exp. Opin. Ther. Patents, 8, p.259–289 [2]. In most of these patents, the synthesised compounds belong to the family of pseudo-peptide derivatives comprising a hydroxamate function. Some patents relate to pseudo-peptide compounds comprising carboxyl-alkyl or thiol functions. In said compounds, the hydroxamate, thiol or carboxyl-alkyl functions interact with the zinc atom present in the active MMP site. The most advanced compounds in terms of anticancer activity have been developed by the firm British Biotechnology. Two compounds, Batimastat BB94 and Marimastat have been the subject of phase II and III clinical studies in humans. Since then, other firms (Roche, Bayer, Agouron, Novartis) appear to have conducted phase I and II clinical studies on MMP inhibitors in cancerology.

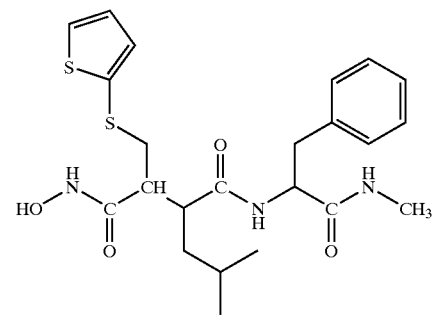

Batimastat, BB94

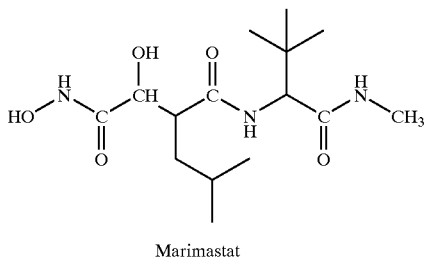

Marimastat

In this way, none of the compounds liable to inhibit MMPs known by means of references [1] and [2], are composed of a phosphinic pseudo-peptide.

However, the document: Goulet et al, Bioorg. Med. Chem. Lett. 4, 1994, p. 1221–1224 [3], describes phosphinic pseudo-peptides that can be used as a selective inhibitor of stromelysin-1 (MMP-3), which comprise the final sequence:

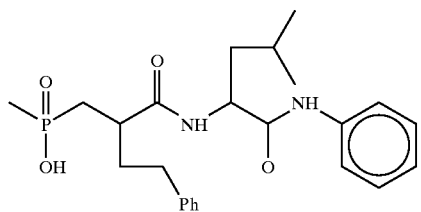

Caldwell et al, Bioorg. Med. Chem. Letter 6, 1996, p.323–328 [4], also describe a phosphinic pseudo-peptide which is a selective inhibitor of stromelysin-1 (MMP-3), which comprises the same terminal sequence as the pseudo-peptide of reference [3].

In these references [3] and [4], it is attempted to detect activity with respect to MMP-3, while in the invention, it is attempted to detect a selective activity with respect to MMP-11, MMP-2, MMP-9 and MMP-8. It is also important to note that, in the present invention, $R^3$ is not only a phenylethyl residue. In addition, the invention demonstrates that other substituents in this position give compounds with increased inhibitory power.

The documents FR-A-2 676 059 [5], FR-A-2 689 764 [6] and EP-A-0 725 075 [7] illustrate phosphinic pseudo-peptides showing an inhibitory activity with respect to bacterial collagenases and zinc endopeptidases 24.15 and 24.16.

The present invention specifically relates to new phosphinic pseudo-peptides showing a powerful and specific inhibitory activity with respect to the matrix zinc metallo-proteases MMP-11, MMP-2, MMP-9 and MMP-8.

DESCRIPTION OF THE INVENTION

According to the invention, the phosphinic pseudo-peptide complies with the formula:

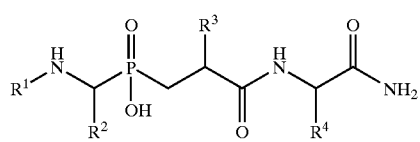

(I)

wherein $R^1$ is a group inhibiting an amine function, or an amino acid residue or peptide with an amino-terminal group protecting function, $R^2$ represents the lateral chain of a natural or non-natural amino acid, $R^3$ represents:
1) the lateral chain of a natural amino acid except for Gly and Ala, not substituted or substituted by an aryl group,
2) an aralkyl group, or
3) an alkyl group comprising at least 3 carbon atoms, and $R^4$ represents a lateral chain of natural or non-natural amino acid, or a dinitrobenzyl group.

Said pseudo-peptide according to formula I is a pseudo-tripeptide comprising a phosphinic type chemical group, the function of which is to chelate the zinc atom in MMPs. In said pseudo-tripeptide, the choice of the $R^2$, $R^3$ and $R^4$ groups makes it possible to ensure the interaction of the tripeptide with the MMP sub-sites S1, S1' and S2', respectively. The $R^1$ group is assumed to interact at the junction of the sub-sites S3/S2.

In the above definition of the pseudo-peptides according to the invention, the terms "amino acid" used for $R^1$, $R^2$, $R^3$ and $R^4$ in [5] refer to the twenty α-amino acids commonly found in proteins which are also known as standard amino acids and their analogues. The lateral chains of said amino acids comprise linear and ramified alkyl, hydroxyalkyl, carboxyalkyl, aralkyl, aminoalkyl, carboxamide alkyl, mercapto alkyl, phenylalkyl, hydroxyphenylalkyl, guanidinoalkyl, imidazoylalkyl, indolylalkyl, and pyrrolidinyl groups.

Examples of amino acid that may be used include alanine, arginine, asparagine, aspartic acid, cysteine, glutamine, glutamic acid, glycine, histidine, iso-leucine, leucine, norleucine, lysin, methionine, phenylalanine, proline, hydroxyproline, serine, threonine, tryptophan, tyrosine, valine, nitrophenylalanine, homo-arginine, thiazolidine and dehydroproline.

However, in the case of $R^3$, the amino acid cannot be Gly or Ala since they do not show sufficient interaction with the MMP sub-site S1'.

Preferentially, the amino acid used for $R^3$ is chosen from Phe, Leu or Ser, Cys residues wherein the lateral chain is substituted by an arylalkyl group.

The aryl groups liable to be used are those derived from a monocyclic or polycyclic aromatic core, possibly substituted by alkyl or alcoxy groups. Examples of aryl groups that may be used include the phenyl, naphthyl, benzyl and alcoxybenzyl groups, such as p-methoxybenzyl.

$R^3$ may also represent an aralkyl group. In said aralkyl group, the aryl group may be any of the other mentioned above. The alkyl part of the aralkyl group may be a linear or ramified chain of 1 to 6 carbon atoms.

Examples of the aralkyl groups that may be used include groups according to the formulas:

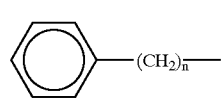

(II)

where n is an integer from 1 to 4, and

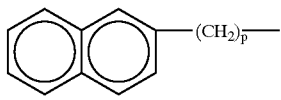
(III)

where p is equal to 1 or 2.

The alkyl groups that may be used for $R^3$ have at least 3 carbon atoms. They may be linear or ramified and preferentially have at most 7 carbon atoms. Examples of alkyl groups that may be used include the groups $CH_3—(CH_2)_6—$ and $(CH_3)_2—CH—CH_2—$.

Preferentially, $R^3$ represents a group complying of any of the following formulas:

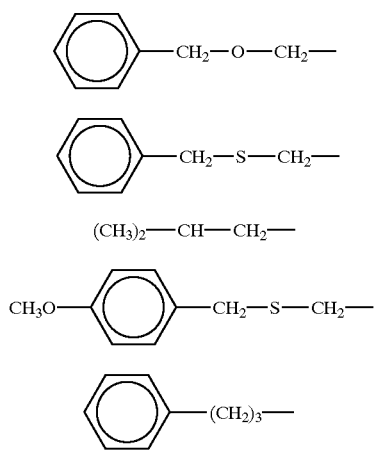

(IV)

(V)

(VI)

(VII)

(VIII)

According to the invention, $R^2$ is chosen so as to interact with the MMP sub-site S1. Good results are obtained when $R^2$ represents the methyl or benzyl group; preferentially, $R^2$ is the benzyl group, which corresponds to the lateral chain of Phe.

According to the invention, $R^4$ is chosen so as to interact with the MMP sub-site S2'. Good results are obtained when $R^4$ represents the lateral chain of Trp or a dinitrobenzyl group Dpa.

In the pseudo-peptide according to the invention, the lateral chains $R^2$, $R^3$ and $R^4$ of the amino acids may be in L or D form. In addition, the pseudo-peptide may be composed of a single isomer or by a mixture of 4-diastereoisomers due to the presence of two asymmetrical centres on the α carbon comprising the $R^2$ and $R^3$ residues. Although any amino acid configuration may be suitable, it is preferable that the unit:

has an L configuration.

However, three out of four diastereoisomers corresponding to different $R^2$ and $R^3$ configurations have practically equivalent activities as MMP inhibitors.

In the pseudo-peptides according to the invention, $R^1$ may represent various groups, the nature of which influences the affinity of the pseudo-peptide with respect to the different MMPs.

$R^1$ may represent a "group inhibiting an amine function". These terms include all the inhibiting groups that may be used to inhibit the amine functions of amino acids and peptides, for example t-butoxy-carbonyl, benzyloxycarbonyl, cinnamoyl, pivalolyl and N-(l-fluorenyl-methoxycarbonyl) Fmoc groups.

$R^1$ may also represent inhibiting groups chosen from the acetyl, benzyloxyacetyl, phenylaminoacetyl, (m-chlorophenyl)aminoacetyl, (2-hydroxy-5-chloro-phenyl) amino acetyl, indolyl-2-carbonyl, 4,6-dichloro-indolyl-2-carbonyl, quinolyl-2-carbonyl and 1-oxa-2,4-dichloro-7-naphthalene carbonyl groups, or an amino acid or peptide residue wherein the terminal amine function is inhibited by a suitable group. Examples of such residues include the Z-Ala and Z-Leu groups wherein Z represents the benzyloxycarbonyl group.

The pseudo-peptides according to the invention may be prepared using conventional methods from phosphinic blocks according to the formula:

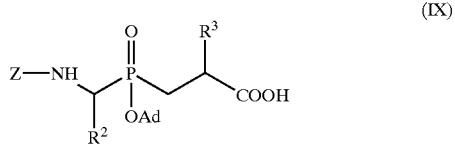
(IX)

wherein Z represents the benzyloxycarbonyl group and Ad the adamantyl group, and the amino acid corresponding to $R^4$ by solid phase chemical synthesis according to the methods described by Yotakis et al, J. Org. Chem., 1996, 61, page 6601–6605 [8] and Jiracek et al, J. Biol. Chem., 1995, 270, p. 21701–21706 [9] and J. Biol. Chem., 1996, 271, p. 19606–19611 [10].

The initial phosphinic blocks may be obtained by Michael addition of a phosphinic acid comprising the $R^2$ group

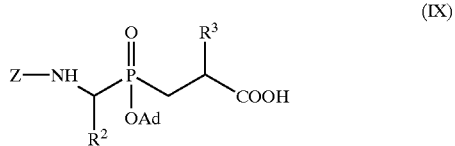
(IX)

on an acrylate supplying the $R^3$ group

(X)

where Et represents the ethyl group.

The acrylates supplying the $R^3$ group may be synthesised using different processes, as seen below.

The pseudo-peptides according to the invention may be used in the treatment of diseases involving an over-expression of matrix zinc metalloproteases.

The invention also relates to a pharmaceutical formulation inhibiting at least one matrix zinc metalloprotease, comprising at least one pseudo-peptide according to formula I as defined above.

Preferentially, said formulation inhibits a matrix zinc metalloprotease chosen from MMP-2, MMP-8, MMP-9 and MMP-11.

Said formulation is intended to treat a disease characterised by the over-expression of matrix proteases, such as cancer.

The invention also relates to the use of a phosphinic pseudo-peptide according to formula I as defined above, to manufacture a medicinal product inhibiting at least one matrix zinc metalloprotease, particularly MMP-2, MMP-8, MMP-9 and MMP-11.

The invention's other characteristics and benefits will be seen more clearly upon reading the following description, naturally given as a non-restrictive illustration, in relation to the appended figures.

DETAILED DESCRIPTION OF EMBODIMENTS

Examples 1 to 27 below illustrate the production of pseudo-peptides according to the invention.

Figure 1:
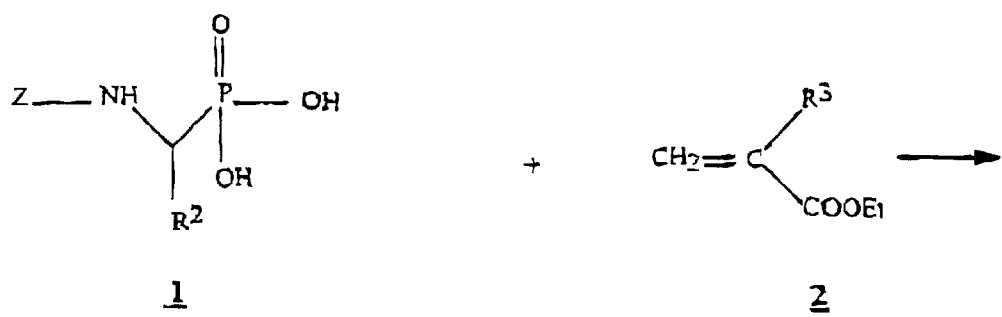
FIG. 1 is a synthesis diagram of pseudo-peptides according to the invention.
Figure 1:
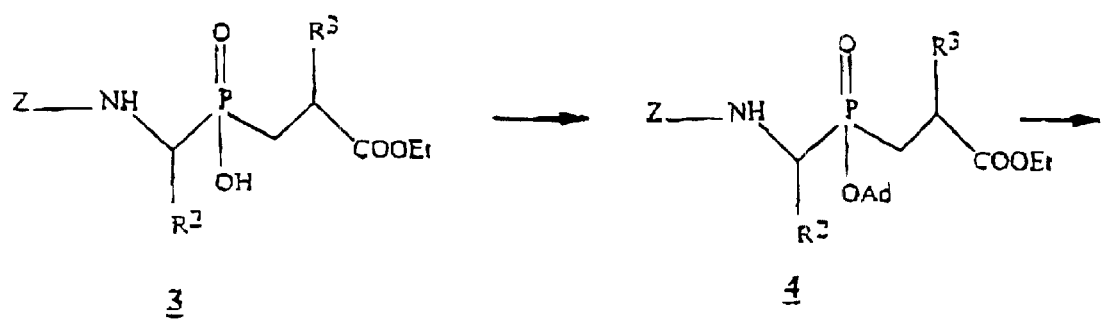
Figure 1:
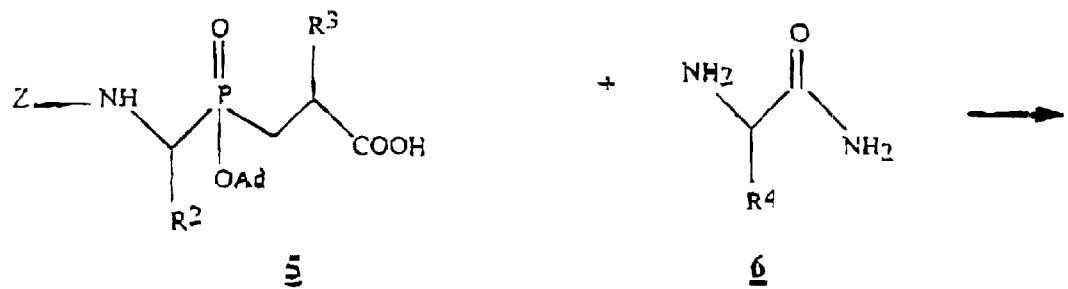
Figure 1:
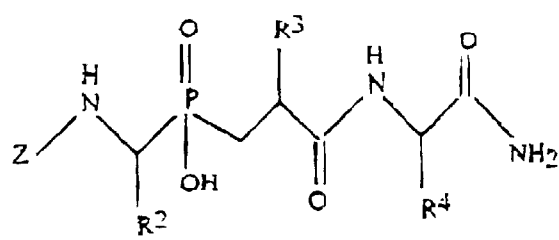

FIG. 1 represents the synthesis diagram of the pseudo-peptides according to the invention, which involves a first reaction to produce phosphinic blocks 3 from a phosphinic acid 1 comprising the R$^2$ group and acrylate 2 supplying the R$^3$ group, by means of Michael addition.

After the formation of the phosphinic block 3, an adamantyl group is introduced on the hydroxyphosphinyl function of the block 4, and the C-terminal ester function 5 is then eliminated, and solid phase synthesis of the pseudo-peptide is performed by adding the required amino acid 6 on the C-terminal acid function.

In this figure, Z represents the benzyloxycarbonyl group.

EXAMPLES 1 to 5

These examples illustrate the preparation of acrylates 2 comprising one R$^3$ group with terminal CH$_2$ using the following method:

Process A:

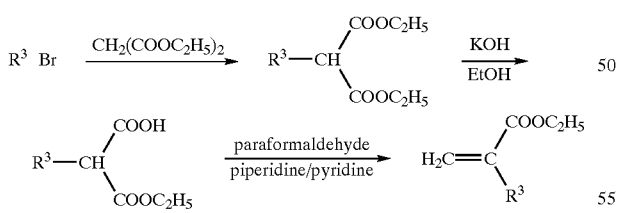

This synthesis corresponds to the method described by Eistetter et al in J. Med. Chem., 25, p109–113, 1982 [11].

This synthesis is described below in the case where R$^3$ represents the groups illustrated in table 1.

To a solution of sodium ethoxide (10 mmol of sodium in 11 ml of pure ethanol), over a period of 10 minutes, 10 mmol of diethyl malonate is added. The solution is placed under stirring at 50° C., for 1 hour, and 10 mmol of the required bromide is then added drop by drop. The mixture is placed under stirring under stirring for 6 hours at 50° C., and the ethanol is eliminated in a vacuum and diethyl ether is added. This solution is washed with water, brine and dried on Na$_2$SO$_4$, and then concentrated to obtain an oily residue, which after distillation gives the diester according to the formula:

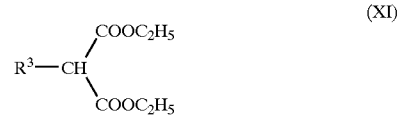

(XI)

with 40 to 65% yields.

To a 10 mmol diester solution in 8 ml of ethanol, a KOH solution (10 mmol) in 8 ml of ethanol is added, and the mixture is stirred for 16 hours. After the organic solvent has evaporated, the residue is treated with water and extracted with diethyl ether.

The aqueous phase is acidified with 6N HCl and extracted twice with diethyl ether. The organic phases are dried on Na$_2$SO$_4$ and evaporated to obtain monoesters according to the formula:

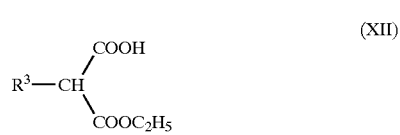

(XII)

with 65 to 90% yields.

To a monoester solution in 0.8 ml of pyridine and 0.05 ml of piperidine, 6 mmol of paraformaldehyde is added, and the mixture is then placed under stirring and heating at 50–55° C. for 3 hours. After adding diethyl ether, the organic phase is washed with water and 3N HCl, and then dried on Na$_2$SO$_4$, and concentrated to obtain compounds 2a to 2c in the table with the yields indicated in said table.

The melting points of the acrylates 2a to 2e obtained are also given in table 1.

EXAMPLE 6

In this example where R$^3$ represents CH$_2$R$'^3$, the acrylate is synthesised according to the following synthesis process:

Process B:

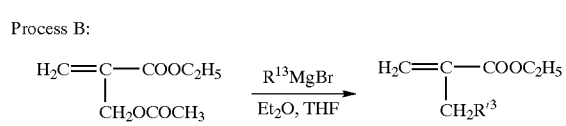

In this example, this synthesis process is used to prepare the acrylate 2 wherein R$^3$ represents the CH$_3$(CH$_2$)$_6$ group, i.e. R$'^3$=CH$_3$—(CH$_2$)$_5$. In an argon atmosphere, a hexyl bromide solution CH$_3$(CH$_2$)$_5$ Br(1.65 g, 10 mmol) in 15 ml of pure diethyl ether is added drop by drop to a flask containing 0.22 g (11 mmol) of magnesium and iodine I$_2$ (catalytic) over a 90 minute period.

The reaction mixture is reflux boiled for 1 hour. After adding 0.18 mmol of CuI, the temperature of the mixture is decreased to −78° C.

A solution of 1.15 g (6.7 mmol) of the compound is then added slowly:

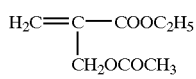
(XIII)

in 10 ml of Et$_2$O: THF. The mixture is stirred for 30 minutes at ambient temperature. After treating the mixture with 0.5N HCl, 5% NaHCO$_3$ and water, the organic layer is dried on Na$_2$SO$_4$. The solvent is eliminated in a vacuum and the residue obtained is purified by column chromatography using a 40 to 60° C. petroleum ether/ether mixture (13:1) as the eluent. The compound 2f is obtained in this way with a 40% yield. The characteristics of compound 2f are given in table 1.

EXAMPLE 7

In this example, an acrylate 2 is prepared with $R_3$=$R'^3$—CH$_2$— using the method described by Baldwin et al J. Chem. Soc. Chem. Comm. 1986, p 1339–1340, [12].

This corresponds to the following reaction diagram:

Process C:

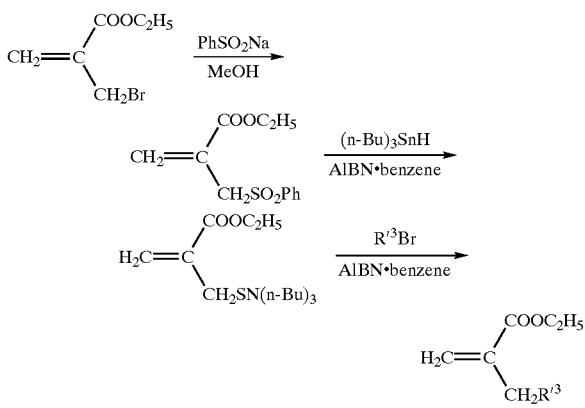

This method is used to prepare the acrylate 2 g wherein $R^3$ represents the group according to the formula:

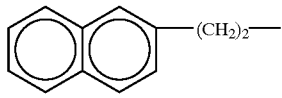
(XIV)

A mixture of 1.9 g (10 mmol) of ethyl bromomethyl acrylate and 3.3 g (20 mmol) of sulphinic benzene acid sodium salt in 40 ml of methanol is reflux boiled for 12 hours. The solvent is eliminated and diethyl ether is added. The solution is washed with water, brine, dried on Na$_2$SO$_4$ and concentrated to obtain 2 grams of sulphinic acrylate

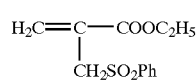
(XV)

in oil form, with an 80% yield.

To a mixture of 2 g (8 mmol) of sulphinic acrylate in 40 ml of dry benzene, 4.7 g (16.4 mmol) of stannic tri-n-butyl hydride and 0.15 g (0.96 mmol) of 2,2'-azobisisobutyronitrile (AIBN) are added. The mixture is reflux boiled for 1.5 hours, and water is then added and the organic layer extracted is dried on Na$_2$SO$_4$ and concentrated. The unprocessed product is purified by column chromatography, using petroleum ether (40 to 60° C.)/ether (9:1) as an eluent. 2.9 g of alkylstannane is obtained

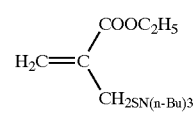
(XVI)

with a 90% yield.

1.47 g (3.6 mmol) of alkylstannane and 0.39 g (1.8 mmol) of 2-bromoethyl naphthalene are dissolved in 10 ml of dry benzene. After adding 0.064 g (0.39 mmol) of AIBN, the reaction mixture is reflux boiled for 2 hours. After adding water, the organic phase is separated, washed with water dried on Na$_2$SO$_4$ and concentrated to dryness. In this way, 0.06 g of the acrylate 2 g given in table 1 is obtained, with a 13% yield, After purifying the residue on a chromatography column using petroleum ether (40 to 60° C.)/ether (9:1) as an eluent.

EXAMPLES 8 AND 9

In these examples, an acrylate 2 is prepared, wherein $R^3$ comprises a sulphur atom or an oxygen atom, according to the following synthesis diagram:

Process D:

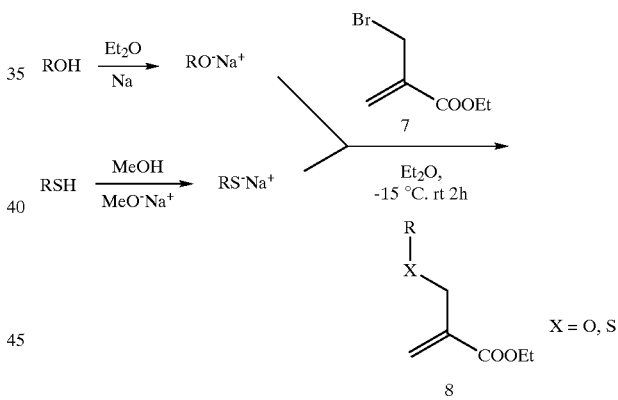

In this diagram, $R^3$ corresponds to RX—CH$_2$ where X=S or O.

The method is used to prepare the acrylates 2h and 2i wherein $R^3$ represents the paramethoxybenzyl-thiomethyl group and the benzylthiomethyl group, respectively.

A 10 mmol solution of suitable thiol R—SH in 15 ml of methanol is added drop by drop to a stirred solution cooled in an ice-bath of 9 mmol of sodium in 20 ml of methanol over a 30 minute period. After adding thiol, the mixture is concentrated to dryness and diethyl ether is added. The salt which precipitates is cooled in an ice-bath. The product is filtered, washed with cold Et$_2$O and dried on P$_2$O$_5$ to obtain the sodium salt with a 85 to 95% yield. To a mixture of 10 mmol of sodium salt in suspension in 40 ml of dry Et$_2$O and cooled in an ice-bath, over a 45 minute period, a solution of ethyl bromomethacrylate (9 mmol) in 20 ml of diethyl ether is added drop by drop. The solution is stirred for 30 minutes at 0° C. and for 1 to 2 hours at ambient temperature. The reaction mixture is diluted with 20 ml of water and the organic layer is washed with water, and then dried on $Na_2SO_4$ and evaporated. The compounds 2h and 2i obtained in this way are purified by column chromatography, using petroleum ether (40–60° C.)/$Et_2O$ (8:2) as an eluent.

The yields are given in table 2.

EXAMPLE 10

In this example, the acrylate 2j wherein $R^3$ corresponds to $ROCH_2$ and represents the group according to the formula $C_6H_4$—$CH_2$—O—$CH_2$ is prepared according to the reaction diagram illustrated above, with R OH.

In a completely dry flask, small pieces of sodium (10 mmol) are added to 20 ml of dry diethyl ether. To this reaction mixture, a 10 mmol solution of benzyl alcohol in 10 ml of diethyl ether is added over a 2 hour period, under a moderate reflux. The mixture is reflux boiled for 6 additional hours. The white precipitate obtained is cooled in an ice-bath, and then filtered, washed with dry and cold diethyl ether and dried on $P_2O_5$ to obtain the sodium salt with an 85 to 95% yield.

The reaction of said salt with ethyl bromomethacrylate and the purification of the compound obtained are performed as described in example 8.

The acrylate 2j obtained is listed in table 2.

EXAMPLES 11 TO 21

In these examples, phosphinic blocks 3 are prepared with $R^2$ and $R^3$ given in table 3, using the procedure described by Yiotakis et al, J. Org. Chem. 61, 1996, 6601–6605 [8].

This procedure firstly comprises the Michael reaction described in FIG. 1. The initial phosphinic acid 1 (FIG. 1) was prepared according to the method described by Baylis et al, J. Chem. Soc. Perkin Trans I, 1984, p. 2845–2853 [13].

The acrylates 2 were prepared in examples 1 to 10. To prepare the phosphinic blocks, proceed as follows.

A suspension of 1 mmol of N-benzoyloxy-carbonylphosphinic acid 1 and 5 mmol of hexamethyldisilazane is heated to 110° C., for 1 hour, in a nitrogen atmosphere.

1.3 mmol of the suitable acrylate 2 is then added drop by drop over a 15 minute period. The reaction mixture is placed under stirring for 3 additional hours at 110° C. The mixture is allowed to cool to 70° C. and 3 ml of ethanol is added drop by drop. After cooling to ambient temperature, the reaction mixture is concentrated. The residue is purified by column chromatography using a chloroform/methanol/acetic acid (7:0.5:0.5) mixture as an eluent. In this way, the phosphinic blocks 3a to 3k are obtained with the yields given in table 3.

In this table, the $R^3$ column indicates which acrylate 2 was used for the synthesis of the phosphinic block. Table 3 also gives the Rf of the blocks obtained.

EXAMPLES 22 AND 23

In these examples, the phosphinic blocks 3l and 3m complying with the formulas given in table 3 are synthesised using the following procedure.

2.1 mmol of diisopropylamine and 2.1 mmol of trimethylsilyl chloride are added to a solution chilled in ice of 1 mmol of phosphinic acid 1 in 2 ml of chloroform.

The mixture is placed under stirring at ambient temperature for 3 hours. After cooling to 0° C., 1.4 mmol of suitable ethyl acrylate 2 (2e or 2g) is added, and the reaction mixture is stirred at ambient temperature for 16 hours. After adding ethanol drop by drop, the solvents are eliminated in a vacuum. The compounds 3l or 3m in table 3 are obtained after column chromatography as for examples 11 to 21.

The yields and Rf values of the blocks obtained are given in table 3.

In addition, the blocks 3b, 3d and 3e to 3k were characterised with proton NMR, carbon 13 and phosphorus. The results obtained are appended.

EXAMPLE 24

In this example, the compounds 4a to 4m in FIG. 1 are prepared from compounds 3a to 3m according to the following procedure.

1 mmol of compound 3a to 3m and 1.2 mmol of 1-adamantyl bromide are dissolved in 10 ml of chloroform. The reaction mixture is reflux boiled. 2 mmol of silver oxide is then added in five equal parts, over a 50 minute period. The solution is reflux boiled for 30 more minutes. After the solvents are eliminated, the residue is treated with diethyl ether and filtered on Celite. The filtrates are concentrated. The residue is purified by column chromatography, using the chloroform/isopropanol (9.8:0.2) mixture as an eluent. In this way, the compounds 4a to 4m are obtained with the yields given in table 4, the Rf values of said compounds are also given in table 4.

EXAMPLE 25

In this example, the procedure described in FIG. 1 is followed to convert compounds 4a to 4m into compounds 5a to 5m. For this purpose, the following procedure is used.

1 ml of 4N NaOH is added drop by drop to a stirred solution of 1 mmol of compound 4a to 4m in 5.5 ml of methanol. The reaction mixture is stirred for 18 hours, and the solvent is then eliminated. The residue is diluted with water, and then acidified with 0.5 N HCl in an ice bath, dried on $Na_2SO_4$ and concentrated to obtain compounds 5a to 5m in white solid form, with the yields given in table 5. The Rf values of said compounds are also given in table 5.

EXAMPLE 26

In this example, phosphinic pseudo-peptides wherein the formulas are given in tables 5 to 7 are prepared from the phosphinic blocks in table 4, by means of Fmoc (fluorenylmethoxycarbonyl) chemistry solid phase synthesis, according to the procedure described by Yotakis et al, 1996, J. Org. Chem. 61, pages 6601–6605 [8] and Jiracek et al in J. Biol. Chem., 1995, 270, pages 21701–21706 [9] and in J. Biol. Chem., 1996, 271, pages 19606–19611 [10].

The coupling is carried out by means of the in situ strategy using 2-(1H-benzotriazol-1-yl-1,1,3,3-tetramethyluronium-hexafluorophosphate(HBTU)/diiso-propylethylamine. The coupling conditions are as follows: three equivalents of amino acid Fmoc derivative and 4 equivalents of diisopropylethylamine in dimethylformamide are added to the resin and left to react for 30 min. For the coupling of the phosphinic blocks:

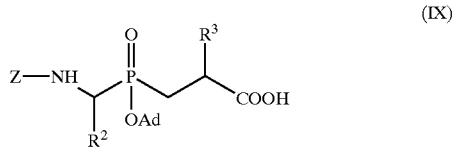

(IX)

1.5 block equivalents are used.

The splitting conditions of the Fmoc group are 50% piperidine in dimethylformamide for 30 minutes. The Fmoc group is (fluoremylmethoxy) carbonyl.

EXAMPLE 27

In this example, the pseudo-peptides given in table 8 comprising different types of $R^1$ group are synthesised. The R¹ group introduction conditions are given below, according to the type of group.

If R¹ is an acid comprising an indole or quinoline group (compounds 30, 31, 32, 33 in table 8), the R¹ group was coupled on the peptide of the generic formula

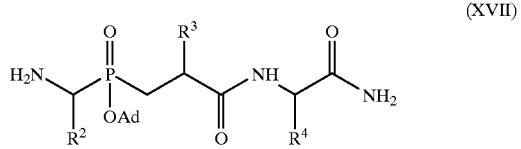

(XVII)

still coupled to the resin, under the following conditions: 3 equivalents of acid diluted in a small volume of N-methyl-pyrolidone, 3 equivalents of HBTU (0.4 M), 10 equivalents of diisopropylethylamine (1.2 M), with a coupling time of 45 min. The incorporation of the R¹ group is followed by a Kaiser test. When required, this operation was repeated several times, until the amine function was completely substituted.

The R¹=Ph—CH₂—O—CH₂—CO— (compound 26) group was incorporated using the corresponding chlorinated derivative under the following conditions: the chlorinated derivative (25 equivalents, 0.5 M/dichloromethane) and diisopropylethylamine (25 equivalents, 0.5 M/dichloromethane) are added to the resin. The acylation reaction requires 1/2 h.

For the synthesis of compounds 27, 28 and 29, the peptide

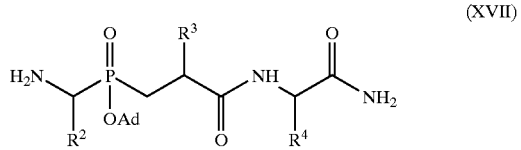

(XVII)

still coupled to the resin, was firstly acylated with the Br—CH₂—CO—Br derivative under the following conditions: the brominated derivative (25 equivalents, 0.5 M/dichloromethane) and diisopropylethylamine (25 equivalents, 0.5 M/dichloromethane) are added to the resin, for a reaction time of 1/2 h. The second step corresponds to the alkylation of the corresponding aniline derivatives. For this purpose, the aniline derivative (50 equivalents/DMSO) is added to the resin, for a coupling time of 2.5 h.

The splitting of the peptides of the resin, and the hydrolysis of the protective groups were carried out using a trifluoroacetic acid solution containing 2.5% water, 2.5% thioanisoi, 1.25% thiophenol, 1.25% ethanedithiol and 1.25% triisopropylsilane.

All the peptides synthesised in examples 26 and 27 were purified by reverse phase HPLC using gradients produced with water, acetonitrile solutions containing 0.01% trifluoroacetic acid. In the majority of cases, four peaks are observed in the chromatograms, corresponding to the four forms of diastereoisomers generated by the synthesis protocol of said phosphinic compounds. All the phosphinic peptides purified in this way were inspected using mass spectroscopy.

EXAMPLE 28

In this example, the affinity constant Ki of the pseudo-peptides in tables 5 to 8 are examined with respect to the different matrix metalloproteases MMP.

The MMPs used were produced in recombinant form, in an *E. coli* expression system, and then purified using different types of chromatographies. Apart from stromelysin-3 (MMP-11), the MMPs produces correspond to human sequences. The Stromelysin-3 used in this study corresponds to the murine form.

The activity of each MMP was determined using two fluorogenic synthetic substrates. The cutoff of said substrates, which generates a fluorescent signal proportional to the quantity of split substrate, enables a precise determination of the kinetic parameters. The values of the constants Km of the substrates, taken into account to determine the Ki values, are given in the table below. The affinity constants Ki were calculated using the equation of Horowitz et al, Proc. Natl. Acad. Sci. USA, 1987, 84, p. 6654–6658 [14], accounting for the dependency of the percentage of inhibition measured experimentally according to the concentration of inhibitor, as a function of the enzyme and substrate concentration.

The experiments for conducted in a Tris/50 mM HCl buffer, pH 6.8, 10 mM $CaCl_2$, 25° C.

| type of MPP | Km $\mu$M |
| --- | --- |
| MMP-11 | 0.2 |
| MMP-2 | 58 |
| MMP-9 | 13 |
| MPP-14 | 26 |
| MMP-1 | 93 |
| MMP-7 | 86 |
| MMP-8 | 60 |

The results obtained are given in tables 5 to 8.

The generic formula of the inhibitors synthesised in this case indicates that they are phosphinic pseudo-tripeptides. According to the assumed bonding mode of said compounds with the MMPs' active site, said inhibitors must interact with the sub-sites S1, S1' and S2' of said enzymes, respectively. The R1group comprised on most of the inhibitors is assumed to interact with the junction of sub-sites S3/S2.

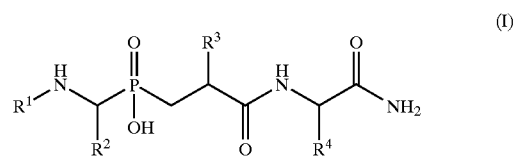

(I)

In table 5, the influence of the type of R³ residue on the efficacy of the pseudo-peptide as an MMP inhibitor.

The interaction of the inhibitors with the sub-site S1', involving the R³ group of the compounds, was the subject of an in-depth study, since this sub-site is thought to mainly control enzyme-inhibitor interaction selectivity.

The analysis of table 5 demonstrates that the size and nature of the R³ residue plays a critical role in the affinity of compounds: in this way, the activity of the inhibitors appears to be multiplied by a factor of 30 in the case of MMP-8, when the R³ group changes from a benzyl to phenylpropyl residue (compounds 7 and 9). It is noted that the gain in affinity corresponding to this substitution is not constant for the different MMPs, suggesting that the sub-site S1' of each MMP may be sensitive to the nature of the R³ residue. In this respect, it is interesting to observe that MMP-11 is the only MMP to prefer phenethyl residue, in relation to a phenylpropyl residue (compound 8 and 9).

The comparison of compounds 9, 10 and 11 which only differ by a single atom (C, O, S) on the R³ residue, suggests the existence of a specific interaction between the sulphur atom in the γ position of $R^3$ of the inhibitors and the sub-site S1' of the MMPs. Irrespective of the type of MMP, compound 11 is always the most powerful of these three inhibitors.

In table 6, the inhibitors are characterised by the presence of a phenyl residue in $R^2$, instead of a methyl residue (table 5). The comparison of tables 5 and 6 reveals that the presence of a benzyl residue makes it possible to increase the overall affinity of the inhibitors. In the specific case of MMP-11, the methyl->benzyl substitution induces a much more significant increase for this MMP, than for the others. This result indicates the preference of the sub-site S1 of MMP-11 for a benzyl residue, in relation to a methyl residue.

Introducing a greater diversity in $R^3$ in this series made it possible to obtain a clearer idea of the influence of the residue in $R^3$. This series demonstrates that, to obtain powerful phosphinic inhibitors with respect to certain MMPs, in the $R^3$ position, it is necessary to introduce a long arylalkyl chain. In this way, compound 18 is an example of a very powerful inhibitor of MMP-8, MMP-11, MMP-2 and MMP-9.

In relation to these MMPs, it is noted that the inhibitors reported in this study appears to be less powerful with respect to MMP-14.

In addition, as a general rule, these pseudo-peptides appear to have a low activity with respect to MMP-1 and MMP-7.

It should be noted that compound 14 comprising a phenethyl $R^3$ residue appears to be very powerful on MMP-11, but it is much less active on other MMPs.

Table 7 illustrates the importance of the tryptophan residue on the $R^4$ position, and the importance of the tryptophan residue configuration. Compound 24 indicates that the tryptophan in these inhibitors may be replaced by another aromatic residue Dpa (dinitrobenzyl) in the case of MMP-11 and MMP-8

Table 8 illustrates the effect of different modifications on the $R^1$ group (Table IV). The analysis of the results indicates that the nature of $R^1$ influences the affinity of compounds with respect to different MMPs. Compound 31 is an example of a very powerful inhibitor with respect to MMP-11, showing a certain selectivity for said enzyme. Compounds 34 and 35 represent examples of powerful inhibitors wherein $R^1$ corresponds to a natural amino acid.

EXAMPLE 29

In this example, the influence of the configuration of the two positions $R^2$ and $R^3$ on the efficacy of pseudo-peptides as an MMP inhibitor is studied.

The synthesis process used in the above examples to prepare the phosphinic derivatives according to this patent produces each inhibitor in the form of a mixture of four diastereoisomers, due to the presence to two asymmetric centres on the alpha carbon comprising the $R^2$ and $R^3$ residues. To evaluate the influence of the configuration of these two positions, compound 15 was resynthesised using optically pure phosphinic phenylalanine amino acid, of an R or S configuration. Each synthesis produces a mixture of two diastereoisomers:

Z-(S)PheY(PO$_2$CH$_2$) (S)pPhe-Trp-NH$_2$ and Z-(S)PheY(PO$_2$CH$_2$) (R)pPhe-Trp-NH$_2$ or Z-(R)PheY(PO$_2$CH$_2$) (S)pPhe-Trp-NH$_2$ and Z-(R)PheY(PO$_2$CH$_2$) (R)pPhe-Trp-NH$_2$ that can easily be separated by reverse phase HPLC. Table 9 shows the activity of the four diastereoisomers of compound 15 with respect to the different MMPs. It is interesting to note that for this class of phosphinic compounds, at least three diastereoisomers inhibit the different MMPs in an almost equivalent manner. This property, apart from being a means to control inhibitor selectivity, could also prove to be very important in terms of metabolism and pharmacokinetics, two parameters which could be sensitive to the molecular stereochemistry.

The results of the characterisation by proton NMR, carbon 13 and phosphorus of the RI fraction of compound 15 are appended.

EXAMPLE 30

In this example, the anti-tumour efficacy of compound 15 (RI fraction) in table 9 (RXPO3) is measured.

The tumorigenesis model used to test the effect of said RXPO3 inhibitor in vivo consists of a subcutaneous graft of malignant murine C26 cells in syngenic mice (with a genetic background similar to that of the injected cells).

The C26 cells established from Balb c mouse colic cancer (Corbett et al., 1975, Cancer Res, 35:2434–2439 [15] are cultured until subconfluence. After trypsinisation, the cells are centrifuged at 1000 g for 10 minutes. The sediment is washed and resuspended in 1×PBS. A 200 ml volume, containing 5×10$^4$ C26 cells, is injected subcutaneously at 2 sites on the back of 8 to 9-week old mice. The inhibitor is solubilised in 1× PBS and 150 mg of inhibitor in a 150 ml volume is administered by the intraperitoneal route. The treatment starts on the day of the injection of the C26 cells and continues at a rate of one injection a day for 25 days. The tumoral volumes are measured every day.

Three identical and independent tumorigenesis experiments were conducted, according to the protocol given above. The results obtained were similar. One of them is reported below.

Figure 2:
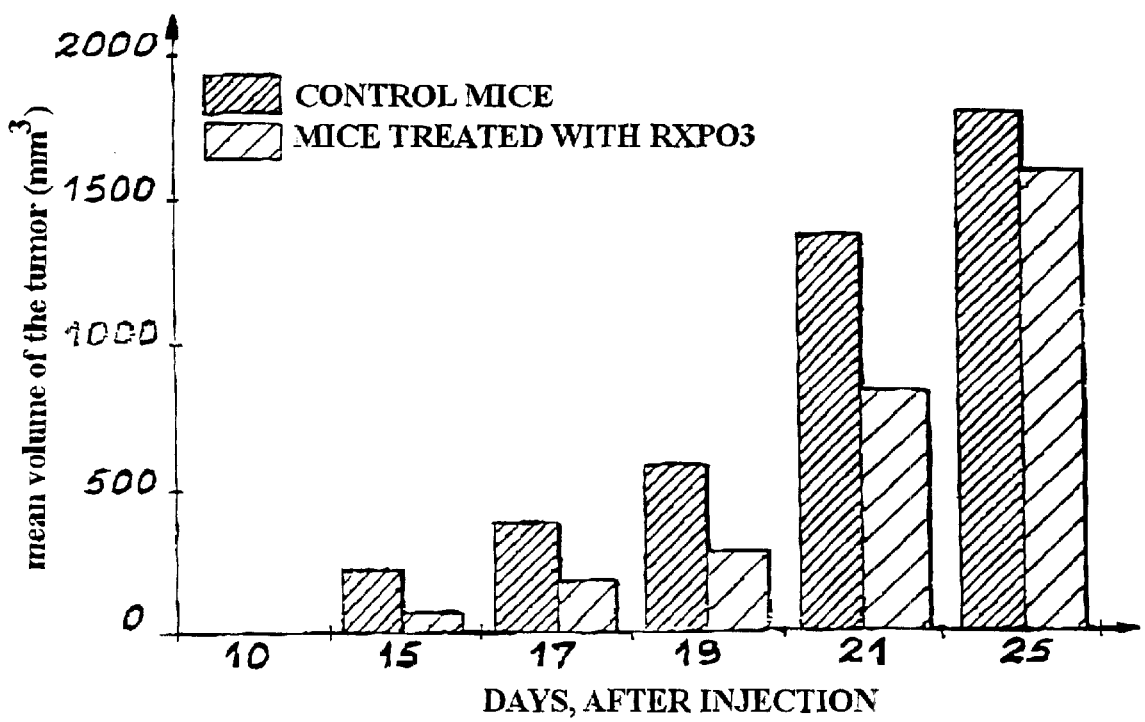
FIG. 2 is a diagram illustrating the anti-tumoral efficacy of a compound according to the invention, which gives the mean volume of the tumour (in mm$^3$) as a function of time (in days) after injecting cancerous cells in control mice and mice treated with the pseudo-peptide according to the invention.

The experiment related to 12 animals, 6 receiving a treatment (150 μg of inhibitor/mouse/day) and 6 used as controlled animals (150 μl 1×PBS). FIG. 2 shows the median values of the tumoral volumes as a function of the time elapsed since the injection of the C26 cells (Days 10 to 25).

It is observed that the tumours start to appear on day D10, and that their mean and median volumes are always lower in the animals treated with the inhibitor RXPO3. This difference in tumour size is of the order of 50% on day D15 to day D20. Subsequently, the efficacy of the inhibitor appears to be lower. These results are in line with the recent observations made on another tumorigenesis model using wild or deficient animals for the expression of stromelysin-3 (MMP-11) and demonstrating that this matrix metalloprotease is involved in the initial implantation steps and favours the development of tumours. According to this model, the efficacy of the inhibitors must be maximal during the first days of tumour development.

References

[1]: Brown, Medical Oncology, 1997, 14, p. 1–10.

[2]: Beckett et al, 1998, Exp. Opin. Ther. Patents, 8, p. 259–289.

[3]: Goulet et al, Bioorg. Med. Chem. Lett. 4, 1994, p. 1221–1224.

[4]: Caldwell et al, Bioorg. Med. Chem. Letter 6, 1996, p.323–328.

[5]: FR-A-2 676 059.

[6]: FR-A-2 689 764.
[7]: EP-A-0 725 075
[8]: Yotakis et al, J. Org. Chem., 1996, 61, p. 6601–6605.
[9]: Jiracek et al, J. Biol. Chem., 1995, 270, p. 21701–21706.
[10]: J. Biol. Chem., 1996, 271, p. 19606–19611.
[11]: Eistetter et al, J. Med. Chem., 25, p 109–113, 1982.
[12]: Baldwin. et al, J. Chem. Soc. Chem. Comm. 1986, p 1339–1340.
[13]: Baylis et al, J. Chem. Soc. Perkin Trans I, 1984, p. 2845–2853.
[14]: Horowitz et al, Proc. Natl. Acad. Sci. USA, 1987, 84, p. 6654–6658.
[15]: Corbett et al., 1975, Cancer Res, 35:2434–2439.

TABLE 1

Acrylate according to the formula:

$$CH_2=C(R^3)-COOC_2H_5$$

| Ex. | compound | $R^3$ | Pf (mm Hg) °C. | Yield (%) |
|---|---|---|---|---|
| 1 | 2a | $C_6H_5CH_2-$ | 64–65 (0.01) | 80 |
| 2 | 2b | $C_6H_5-(CH_2)_2-$ | 90–95 (0.7) | 76 |
| 3 | 2c | $C_6H_5(CH_2)_3-$ | 112–115 (0.6) | 87 |
| 4 | 2d | $C_6H_5(CH_2)_4-$ | 120–125 (0.005) | 78 |
| 5 | 2e | naphthyl-$CH_2-$ | Oil | 25 |
| 6 | 2f | $CH_3(CH_2)_6-$ | 101–105 (8) | 40 |
| 7 | 2g | naphthyl-$(CH_2)_2-$ | Oil | 13 |

TABLE 2

Acrylate according to formula:

$$CH_2=C(R^3)-COOC_2H_5$$

| Ex. | compound | $R^3 = R\ X\ CH_2$ where X = O or S. | Yield |
|---|---|---|---|
| 8 | 2h | MeO-$C_6H_4$-$CH_2-S-CH_2-$ | 80% |
| 9 | 2i | $C_6H_5$-$CH_2-S-CH_2-$ | 88% |
| 10 | 2j | $C_6H_5$-$CH_2-O-CH_2-$ | 85% |

TABLE 3

| Ex. | Phosphinic block | $R^2$ | $R^3$ | Yield % | Rf |
|---|---|---|---|---|---|
| 11 | 3a | H | $C_6H_5CH_2$ (2a) | 80 | 0.41 |
| 12 | 3b | H | $C_6H_5-(CH_2)_2$ (2b) | 95 | 0.47 |
| 13 | 3c | H | $C_6H_5(CH_2)_3$ (2c) | 83 | 0.57 |
| 14 | 3d | H | $C_6H_5-CH_2-O-CH_2$ (2j) | 61 | 0.69 |
| 15 | 3e | H | $C_6H_5-CH_2-S-CH_2$ (2i) | 60 | 0.48 |
| 16 | 3f | Phenyl | $C_6H_5(CH_2)_2$ (2b) | 85 | 0.77 |
| 17 | 3g | " | $C_6H_5(CH_2)_3$ (2c) | 79 | 0.80 |
| 18 | 3h | " | $C_6H_5(CH_2)_4$ (2d) | 75 | 0.82 |
| 19 | 3i | " | $CH_3(CH_2)_6$ (2f) | 81 | 0.68 |
| 20 | 3j | " | $C_6H_5-CH_2-O-CH_2$ (2j) | 64 | 0.61 |

TABLE 3-continued

| Ex. | Phosphinic block | R² | R³ | Yield % | Rf |
|---|---|---|---|---|---|
| 21 | 3k | " | 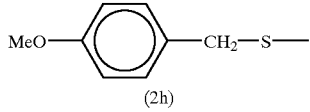 (2h) | 40 | 0.63 |
| 22 | 3l | " | 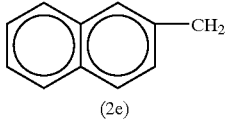 (2e) | 60 | 0.66 |
| 23 | 3m | " | 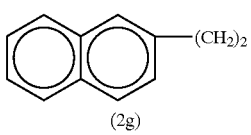 (2g) | 30 | 0.65 |

TABLE 4

| Initial compound | Compound 4 | Yield | Rf¹ | Compound 5 | Yield | Rf² |
|---|---|---|---|---|---|---|
| 3a | 4a | 95 | 0.70 | 5a | 80 | 0.53¹ |
| 3b | 4b | 97 | 0.72 | 5b | 81 | 0.59¹ |
| 3c | 4c | 97 | 0.73 | 5c | 85 | 0.21 |
| 3d | 4d | 93 | 0.77 | 5d | 90 | 0.42¹ |
| 3e | 4e | 72 | 0.72 | 5e | 92 | 0.50¹ |
| 3f | 4f | 89 | 0.61 | 5f | 95 | 0.42 |
| 3g | 4g | 75 | 0.66 | 5g | 97 | 0.42 |
| 3h | 4h | 95 | 0.63 | 5h | 95 | 0.44 |
| 3i | 4i | 96 | 0.78 | 5i | 78 | 0.56 |
| 3j | 4j | 91 | 0.71 | 5j | 80 | 0.26 |
| 3k | 4k | 93 | 0.66 | 5k | 94 | 0.46 |
| 3l | 4l | 91 | 0.53 | 5l | 92 | 0.38 |
| 3m | 4m | 95 | 0.57 | 5m | 86 | 0.35 |

¹in the hexane/ethyl acetate/acetic acid (3:3:0.2) mixture
²in the chloroform/methanol (9.5:0.5) mixture.

TABLE 5

Influence of the R³ group: Value of affinity constants Ki.

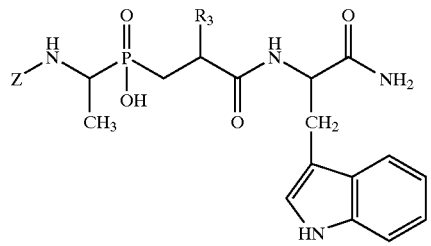

(XVIII)

| Compound No | [R3] = | MMP-11 mST3 | MMP-2 Gel-A | MMP-9 Gel-B | MMP-14 MT1-MMP | MMP-1 HFC | MMP-7 Matrilysin | MMP-8 HNC |
|---|---|---|---|---|---|---|---|---|
| 7 | CH₂-φ (Phe) | 350 nM | 250 nM | 280 nM | 2030 nM | 24% @ 2 mM | 71% @ 0 mM | 240 nM |
| 8 | CH₂—CH₂-f | 51 nM | 80 nM | 60 nM | 270 nM | 23% @ 2 mM | 43% @ 50 mM | 20 nM |
| 9 | CH₂—CH₂—CH₂-f | 100 nM | 31 nM | 23 nM | 92 nM | 30% @ 2 mM | 51% @ 50 mM | 8 nM |
| 10 | CH₂—O—CH₂-f | 175 nM | 250 nM | 44 nM | 550 nM | 15% @ 2 mM | 27% @ 50 mM | 19 nM |
| 11 | CH₂—S—CH₂-f | 36 nM | 14 nM | 6 nM | 26 nM | 45% @ 2 mM | 36% @ 50 mM | <0.5 nM |

TABLE 6

Influence of the $R^3$ group: Value of affinity constants Ki.

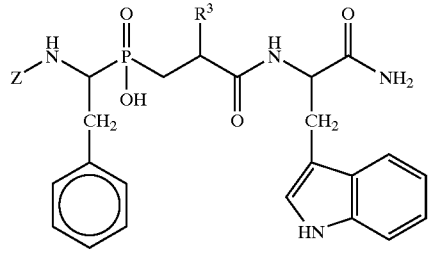

(XIX)

| [R3] = | | MMP-11 | MMP-2 | MMP-9 | MMP-14 | MMP-1 | MMP-7 | MMP-8 |
|---|---|---|---|---|---|---|---|---|
| 12 | $CH_3$ (Ala) | 2670 nM | 0% @ 2 mM | 0% @ 2 mM | 0% @ 10 mM | 20% @ 2 mM | 10% @ 50 mM | 9% @ 1 mM |
| 13 | $CH_3$—CH—$(CH_3)_2$ (Leu) | 22 nM | 202 nM | 65 nM | 192 nM | 45% @ 2 mM | 210 nM | 40 nM |
| 14 | $CH_2$—$CH_2$-φ | 8.8 nM | 275 nM | 110 nM | 660 nM | 10% @ 2 mM | 62% @ 50 mM | 45 nM |
| 15 | $CH_2$—$CH_2$—$CH_2$-φ | 5 nM | 20 nM | 10 nM | 105 nM | 23% @ 2 mM | 65% @ 50 mM | 2.5 nM |
| 16 | $CH_2$—$CH_2$—$CH_2$—$CH_2$-φ | 33 nM | 145 nM | 70 nM | 580 nM | 5% @ 2 mM | 65% @ 50 mM | 4.3 nM |
| 17 | $CH_2$—O—$CH_2$-φ | 16 nM | 85 nM | 55 nM | 545 nM | 9% @ 2 mM | 40% @ 50 mM | 20 nM |
| 18 | $CH_2$—S—$CH_2$-f-OMe | 2 nM | 6 nM | 3 nM | 22 nM | 13% @ 2 mM | 84% @ 50 mM | 0.7 nM |
| 19 | $CH_2$-Naphthyl | 74 nM | 330 nM | 675 nM | 1350 nM | 0% @ 5 mM | 1800 nM | 230 nM |
| 20 | $CH_2$—$CH_2$-Naphthyl | 12 nM | 30 nM | 55 nM | 125 nM | 0% @ 2 mM | 210 nM | 34 nM |
| 21 | $(CH_2)_7$ | 34 nM | 75 nM | 30 nM | 271 nM | 27% @ 2 mM | 50% @ 50 mM | 6 nM |

TABLE 7

Influence of residue in Yaa' position: Value of affinity constants Ki.

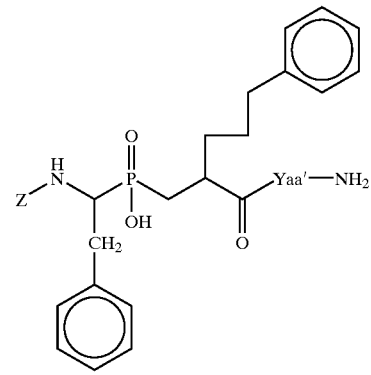

(XX)

| Compound No. | Yaa' | MMP-11 mST3 | MMP-2 Gel-A | MMP-9 Gel-B | MMP-14 MT1-MMP | MMP-1 HFC | MMP-7 Matrilysin | MMP-8 HNC |
|---|---|---|---|---|---|---|---|---|
| 22 | Ala | 20% @ 1 mM | 31% @ 2 mM | 45% @ 2 mM | 2960 nM | 9% @ 2 mM | 23% @ 50 mM | 240 nM |
| 15 | L-Trp | 5 nM | 20 nM | 10 nM | 105 nM | 23% @ 2 mM | 65% @ 50 mM | 2.5 nM |
| 23 | D-Trp | 1% @ 1 mM | 6% @ 2 mM | 14% @ 2 mM | 10% @ 10 mM | 3% @ 10 mM | 18% @ 50 mM | 2% @ 1 mM |
| 24 | Dpa | 27 nM | 260 nM | 245 nM | 1282 nM | 9% @ 2 mM | 61% @ 50 mM | 25 nM |

TABLE 8

Influence of R1 residue: Value of affinity constants Ki.

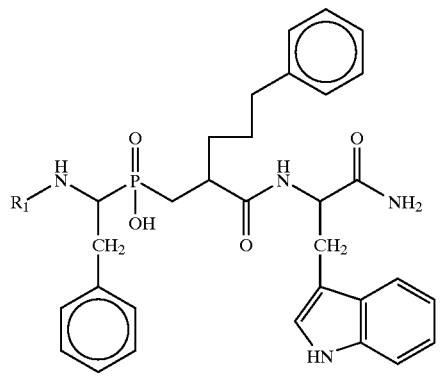

(XXI)

| Compound No. | [R1] = | MMP-11 mST3 | MMP-2 Gel-A | MMP-9 Gel-B | MMP-14 MT1-MMP | MMP-1 HFC | MMP-7 Matrilysin | MMP-8 HNC |
|---|---|---|---|---|---|---|---|---|
| 25 | H₃C-C(=O)- | 20 nM | 26 nM | 35 nM | 90 nM | 29% @ 1 μM | 16% @ 1 μM | 3.5 nM |
| 26 | PhCH₂-O-CH₂-C(=O)- | 5 nM | 8 nM | 10 nM | 40 nM | 28% @ 1 μM | 33% @ 1 μM | 2.5 nM |
| 27 | PhNH-CH₂-C(=O)- | 15 nM | 17 nM | 6 nM | 73 nM | 33% @ 1 μM | 16% @ 1 μM | 4.5 nM |
| 28 | (3-Cl-C₆H₄)NH-CH₂-C(=O)- | 3.8 nM | 9 nM | 6 nM | 45 nM | 63% @ 1 μM | 25% @ 1 μM | 4 nM |
| 29 | (5-Cl-2-OH-C₆H₃)NH-CH₂-C(=O)- | 10 nM | 30 nM | 34 nM | 63 nM | 55% @ 1 μM | 48% @ 1 μM | 7.5 nM |
| 30 | (indol-2-yl)-C(=O)- | 1.5 nM | 10 nM | 8 nM | 41 nM | 87% @ 1 μM | 605 nM | 1? nM |
| 31 | (4,6-dichloroindol-2-yl)-C(=O)- | 0.9 nM | 24 nM | 7 nM | 32 nM | 36 nM | 117 nM | 5 nM |

TABLE 8-continued

Influence of R1 residue: Value of affinity constants Ki.

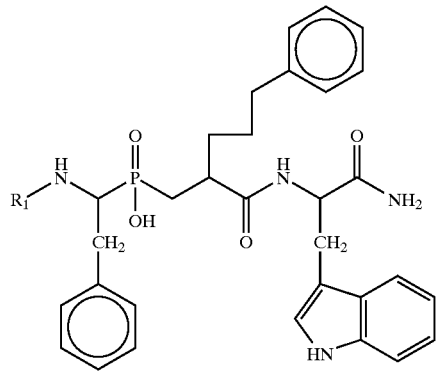

(XXI)

| Compound No. | [R1] = | MMP-11 mST3 | MMP-2 Gel-A | MMP-9 Gel-B | MMP-14 MT1-MMP | MMP-1 HFC | MMP-7 Matrilysin | MMP-8 HNC |
|---|---|---|---|---|---|---|---|---|
| 32 | quinoline-2-carbonyl | 4.2 nM | 19 nM | 13 nM | 60 nM | 78% @ 1 μM | 370 nM | 5 nM |
| 33 | 6,8-dichloro-coumarin-3-carbonyl | 5 nM | 100 nM | 110 nM | 217 nM | 47% @ 1 μM | 37% @ 1 μM | 17 nM |
| 34 | Z-Ala | 8 nM | 11 nM | 10 nM | 41 nM | 24% @ 1 μM | 18% @ 1 μM | 5.5 nM |
| 35 | Z-Leu | 6 nM | 40 nM | 22 nM | 53 nM | 20% @ 1 μM | 32% @ 1 μM | 7 nM |

TABLE 9 influence of R2 and R3 residue configuration: Value of affinity constants Ki.

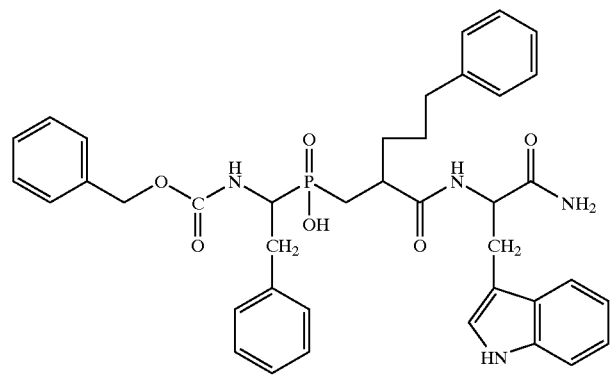

(XXII)

| R2 residue configuration | HPLC fraction | MMP-11 mST3 | MMP-2 Gel-A | MMP-9 Gel-B | MMP-14 MT1-MMP | MMP-1 HFC | MMP-7 Matrilysin | MMP-8 HNC |
|---|---|---|---|---|---|---|---|---|
| S | I | 5 nM | 45 nM | 33 nM | 135 nM | 17% @ 2 mM | 59% @ 20 mM | 16 nM |
| S | II | 50 nM | 365 nM | 250 nM | 2290 nM | 6% @ 2 mM | 29% @ 20 mM | 460 nM |
| R | I | 6 nM | 54 nM | 42 nM | 90 nM | 18% @ 2 mM | 44% @ 20 mM | 16 nM |
| R | II | 9 nM | 42 nM | 78 nM | 385 nM | 16% @ 2 mM | 34% @ 20 mM | 65 nM |

Block 3b: ZAlaΨ(PO₂CpH₂)hPheOEt.

| ¹H | Z | Phe | hPhe | OEt |
|---|---|---|---|---|
| NH | | 5.36 | | |
| Hα | | 4.05 | 2.85 | |
| Hβ | | 1.28 | 1.95/1.84 | |
| Hγ | | | 2.55 | |
| CH₃ | | | | 1.28 |
| Arom | 6.62–7.33 | | 6.62–7.33 | |
| CH₂/CpH₂ | 5.12 | | 1.84/2.25 | 4.1 |

| ¹³C | Z | Phe | hPhe | OEt |
|---|---|---|---|---|
| Cα | | 45.35/46.05* | 39.2 | |
| Cβ | | 14.6 | 35.9 | |
| Cγ | | | 33.4 | |
| CH₃ | | | | 61.4 |
| Arom | 126.4–141.4 | 126.4–141.4 | | |
| C=0 | 156.2 | | 174.9 | |
| CH₂/Cp | 67.6 | | 28.5/27.8* | 14.6 |

*2 diastereoisomers

| ³¹P | 54.45/54.23 |
|---|---|

δ(ppm) Ref. ¹H CHCl₃ (7.26 ppm). Temp.: 298 K. Solvent: CDCl₃
Ref. ¹³C CDCl₃ (77.36 ppm).
Ref. ³¹P H₃PO₄ (0 ppm).

Block 3d: ZAlaΨ(PO₂CpH₂)Ser(Bn)OEt.

| ¹H | Z | Ala | Ser(Bn) | OEt |
|---|---|---|---|---|
| NH | | 5.41 | | |
| Hα | | 4.05 | 3.09 | |
| Hβ | | 1.35 | 3.65 | |
| Hδ | | | 4.48 | |
| CH₃ | | | | 1.2 |
| Arom | 7.26–7.32 | | 7.26–7.32 | |
| CH₂/CpH₂ | 5.09 | | 2.02/2.25 | 4.12 |

| ¹³C | Z | Ala | Ser(Bn) | OEt |
|---|---|---|---|---|
| Cα | | 45.20/46.8* | 40.13 | |
| Cβ | | 14.42 | 71.38 | |
| Cδ | | | 73.5 | |
| CH₃ | | | | 61.77 |
| Arom | 127.9–138.2 | 127.9–138.2 | | |
| C=0 | 156.3 | | 173.2 | |
| CH₂/Cp | 67.64 | | 24.16/25.77* | 14.42 |

*2 diastereoisomers

| ³¹P | 54.3 |
|---|---|

δ(ppm) Ref. ¹H CHCl₃ (7.26 ppm). Temp.: 298 K. Solvent: CDCl₃
Ref. ¹³C CDCl₃ (77.36 ppm).
Ref. ³¹P H₃PO₄ (0 ppm).

Block 3e: ZAlaΨ(PO₂CpH₂)Cys(Bn)OEt.

| ¹H | Z | Ala | Cys(Bn) | OEt |
|---|---|---|---|---|
| NH | | 5.41 | | |
| Hα | | 4.08 | 3 | |
| Hβ | | 1.35 | 2.50/2.75 | |
| Hδ | | | 3.65 | |
| CH₃ | | | | 1.22 |
| Arom | 7.26–7.33 | | 7.26–7.33 | |
| CH₂/CpH₂ | 5.12 | | 2.02/2.25 | 4.15 |

| ¹³C | Z | Ala | Cys(Bn) | OEt |
|---|---|---|---|---|
| Cα | | 44.93/46.7* | 39.19 | |
| Cβ | | 14.4 | 34.56 | |
| Cδ | | | 36.33 | |
| CH₃ | | | | 61.7 |
| Arom | 127.4–138.1 | 127.4–138.1 | | |
| C=0 | 156.17 | | 173.56 | |
| CH₂/Cp | 67.78 | | 26.88/28.19* | 14.43 |

*2 diastereoisomers

| ³¹P | 54.41/54.23 |
|---|---|

δ(ppm) Ref. ¹H CHCl₃ (7.26 ppm). Temp.: 298 K. Solvent: CDCl₃
Ref. ¹³C CDCl₃ (77.36 ppm).
Ref. ³¹P H₃PO₄ (0 ppm).

Block 3f: ZPheΨ(PO₂CpH₂)hPheOEt.

| ¹H | Z | Phe | hPhe | OEt |
|---|---|---|---|---|
| NH | | 5.61 | | |
| Hα | | 4.2 | 2.92 | |
| Hβ | | 3.17/2.83 | 1.97/1.83 | |
| Hγ | | | 2.55 | |
| CH₃ | | | | 1.23 |
| Arom | 7.0–7.3 | 7.0–7.3 | | |
| CH₂/CpH₂ | 5 | | 1.85/2.22 | 4.15 |

| ¹³C | Z | Phe | hPhe | OEt |
|---|---|---|---|---|
| Cα | | 52.1/53.5* | 39.8 | |
| Cβ | | 34 | 35.5 | |
| Cγ | | | 33.1 | |
| CH₃ | | | | 63.05 |
| Arom | 127–141 | 127–141 | | |
| C=0 | 158 | | 177.6 | |
| CH₂/CpH₂ | 68.5 | | 28.9/27.7* | 14.1 |

*2 diastereoisomers

| ³¹P | 51.34 |
|---|---|

δ(ppm) Ref. ¹H CHCl₃ (7.26 ppm). Temp.: 298 K. Solvent: CDCl₃
Ref. ¹³C CDCl₃ (77.36 ppm).
Ref. ³¹P H₃PO₄ (0 ppm).

Block 3g: ZPheΨ(PO₂CpH₂)pPheOEt.

| ¹H | Z | Phe | pPhe | OEt |
|---|---|---|---|---|
| NH | | 4.98 | | |
| Hα | | 4.2 | 2.87 | |
| Hβ | | 3.23/2.83 | 1.53/1.45 | |
| Hγ | | | 1.51 | |
| Hδ | | | 2.52 | |
| CH₃ | | | | 1.21 |
| Arom | 7.14–7.26 | 7.14–7.26 | | |
| CH₂/CpH₂ | 4.94 | | 1.75–2.21 | 4.13 |

| ¹³C | Z | Phe | pPhe | OEt |
|---|---|---|---|---|
| Cα | | 51.75/53.3* | 39.7 | |
| Cβ | | 33.85 | 33.6 | |
| Cγ | | | 28.4 | |
| Cδ | | | 35.7 | |
| CH₃ | | | | 62.3 |
| Arom | 126.6–142.3 | 126.6–142.3 | | |
| C=0 | 157.7 | | 177.2 | |
| CH₂/Cp | 68.3 | | 29.1/28* | 13.9 |

*2 diastereoisomers

| ³¹P | 52.2/53.1 |
|---|---|

δ(ppm) Ref. ¹H CHCl₃ (7.26 ppm). Temp.: 298 K. Solvent: CDCl₃
Ref. ¹³C CDCl₃ (77.36 ppm).

Ref. $^{31}$P H$_3$PO$_4$ (0 ppm).

Block 3h: ZPheΨ(PO$_2$CpH$_2$)bPheOEt.

| $^1$H | Z | Phe | bPhe | OEt |
|---|---|---|---|---|
| NH | | 5.4 | | |
| Hα | | 4.25 | 2.8 | |
| Hβ | | 3.26/2.82 | 1.62/1.53 | |
| Hγ | | | 1.25 | |
| Hε | | | 1.52 | |
| Hδ | | | 2.52 | |
| CH$_3$ | | | | 1.2 |
| Arom | 7.0–7.26 | 7.0–7.26 | | |
| CH$_2$/CpH$_2$ | 4.99 | | 1.75–2.23 | 4.1 |

| $^{13}$C | Z | Phe | bPhe | OEt |
|---|---|---|---|---|
| Cα | | 52.2/50.9* | 39.7 | |
| Cβ | | 34.4 | 34 | |
| Cγ | | | 26.4 | |
| Cδ | | | 31.2 | |
| Cε | | | 35.8 | |
| CH$_3$ | | | | 61.4 |
| Arom | 126.4–142.6 | 126.4–142.6 | | |
| C=0 | 156.5 | | 175.3 | |
| CH$_2$/Cp | 67.45 | | 28.44/29.3* | 14.2 |

*2 diastereoisomers

| $^{31}$p | 52.2/53.1 |
|---|---|

δ(ppm) Ref. $^1$H CHCl$_3$ (7.26 ppm). Temp.: 298 K. Solvent: CDCl$_3$
Ref. $^{13}$C CDCl$_3$ (77.36 ppm).
Ref. $^{31}$P H$_3$PO$_4$ (0 ppm).

Block 3i: ZPheΨ(PO$_2$CpH$_2$)HeptOEt.

| $^1$H | Z | Phe | Hept | OEt |
|---|---|---|---|---|
| NH | | 5.46 | | |
| Hα | | 4.26 | 2.8 | |
| Hβ | | 3.28/2.85 | 1.50/1.63 | |
| Hγ–Hζ | | | 1.2 | |
| CH$_3$ | | | 0.83 | 1.23 |
| Arom | 7.16/7.27 | 7.67–7.27 | | |
| CH$_2$/CpH$_2$ | 4.98 | | 1.75–2.23 | 4.2 |

| $^{13}$C | Z | Phe | Hept | OEt |
|---|---|---|---|---|
| Cα | | 51.25/52.8* | 39.31 | |
| Cβ | | 34.2 | 34.6 | |
| Cγ/Cζ | | | 31.97 · 29.31 | |
| | | | 26.65 · 22.81 | |
| CH$_3$ | | | 14.5 | 61.2 |
| Arom | 127.5–137.6 | 127.5–137.6 | | |
| C=0 | 156.36 | | 175.37 | |
| CH$_2$/Cp | 67.23 | | 29.73/28.45* | 14.6 |

*2 diastereoisomers

| $^{31}$p | 54.41/53.96 |
|---|---|

δ(ppm) Ref. $^1$H CHCl$_3$ (7.26 ppm). Temp.: 298 K. Solvent: CDCl$_3$
Ref. $^{13}$C CDCl$_3$ (77.36 ppm).
Ref. $^{31}$P H$_3$PO$_4$ (0 ppm).

Block 3j: ZPheΨ(PO$_2$CpH$_2$)Ser(Bn)OEt.

| $^1$H | Z | Phe | Ser(Bn) | OEt |
|---|---|---|---|---|
| NH | | 5.48 | | |
| Hα | | 4.3 | 3.12 | |
| Hβ | | 3.28/2.85 | 3.65 | |
| Hδ | | | 4.45 | |
| CH$_3$ | | | | 1.22 |
| Arom | 7.16–7.36 | 7.16/7.36 | | |
| CH$_2$/CpH$_2$ | 4.97 | | 2.0/2.27 | 4.15 |

| $^{13}$C | Z | Phe | Ser(Bn) | OEt |
|---|---|---|---|---|
| Cα | | 52.65/50.9* | 39.93 | |
| Cβ | | 34.16 | 71.42 | |
| Cδ | | | 73.44 | |
| CH$_3$ | | | | 61.6 |
| Arom | 126–138.1 | 126–138.1 | | |
| C=0 | 156.4 | | 173.2 | |
| CH$_2$/Cp | 67.47 | | 24.9/25.36* | 13.94 |

*2 diastereoisomers

| $^{31}$p | 53.7/53.59 |
|---|---|

δ(ppm) Ref. $^1$H CHCl$_3$ (7.26 ppm). Temp.: 298 K. Solvent: CDCl$_3$
Ref. $^{13}$C CDCl$_3$ (77.36 ppm).
Ref. $^{31}$P H$_3$PO$_4$ (0 ppm).

Block 3k: ZPheΨ(PO$_2$CpH$_2$)Cys(pOMeBn)OEt.

| $^1$H | Z | Phe | Cys(pOMeBn) | OEt |
|---|---|---|---|---|
| NH | | 5.41 | | |
| Hα | | 4.3 | 3.03 | |
| Hβ | | 3.27/2.80 | 2.53/2.70 | |
| Hγ | | | 3.6 | |
| CH$_3$ | | | 3.75 | 1.2 |
| Arom | 7.18–7.36 | 7.18–7.36 | | |
| CH$_2$/CpH$_2$ | 4.98 | | 2.03/2.15 | 4.15 |

| $^{13}$C | Z | Phe | Cys(pOMeBn) | OEt |
|---|---|---|---|---|
| Cα | | 52.1/50.8* | 39.6 | |
| Cβ | | 34.42 | 35 | |
| Cδ | | | 35.6 | |
| CH$_3$ | | | 55.98 | 61.74 |
| Arom | 127.2–130.4 | 127.2–130.4 | | |
| C=0 | 159 | | 173.6 | |
| CH$_2$/Cp | 67.32 | | 27.9/29.1* | 14.46 |

*2 diastereoisomers

| $^{31}$p | 53.76/54.07 |
|---|---|

δ(ppm) Ref. $^1$H CHCl$_3$ (7.26 ppm). Temp.: 298 K. Solvent: CDCl$_3$
Ref. $^{13}$C CDCl$_3$ (77.36 ppm).
Ref. $^{31}$P H$_3$PO$_4$ (0 ppm).

Compound 15: ZPheΨ(PO$_2$CpH$_2$)pPheTrpNH$_2$ RI fraction in table 9

| $^1$H | Z | Phe | pPhe | Trp |
|---|---|---|---|---|
| NH | | 5.63 | | 7.05 |
| Hα | | 4.17 | 2.87 | 4.72 |
| Hβ | | 3.13/2.75 | 1.59/1.40 | 3.25 |
| Hγ | | | 1.45 | |
| Hδ | | | 2.46 | |
| CH$_2$/CpH$_2$ | 4.95 | | 1.81/2.06 | |

| $^{13}$C | Z | Phe | pPhe | Trp |
|---|---|---|---|---|
| Cα | | 52 | | 54.7 |
| Cβ | | 33.85 | 34.06 | 27.7 |
| Cγ | | | 28.53 | |
| Cδ | | | 35.63 | |
| C=0 | 158.17 | | 177.19 | 176.93 |
| CH$_2$/Cp | 68.81 | | 28.45 | |

| $^{31}$p | 51.76/52.94 |
|---|---|

δ(ppm) Ref. $^1$H CHCl$_3$ (7.26 ppm). Temp.: 298 K. Solvent: CDCl$_3$

Ref. $^{13}$C CDCl$_3$ (77.36 ppm).
Ref. $^{31}$P H$_3$PO$_4$ (0 ppm).

What is claimed is:

1. Phosphinic pseudo-peptide according to the formula:

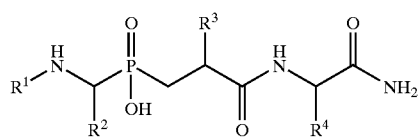
(I)

wherein
- $R^1$ is an amine-protecting group,
- $R^2$ represents the lateral chain of a natural amino acid or an analogue thereof,
- $R^3$ represents:
    1) the lateral chain of a natural amino acid except for Gly and Ala, not substituted or substituted by an aryl group,
    2) an aralkyl group, or
    3) an alkyl group comprising at least 3 carbon atoms, and
- $R^4$ represents the lateral chain of a natural amino acid or an analogue thereof.

2. Pseudo-peptide according to claim 1, wherein $R^2$ represents a methyl or benzyl group.

3. Phosphinic pseudo-peptide according to the formula:

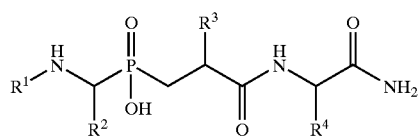
(I)

wherein
- $R^1$ is an amine-protecting group,
- $R^2$ represents the lateral chain of a natural amino acid or an analogue thereof,
- $R^3$ represents the lateral chain of an amino acid selected from the group consisting of Phe, Leu, Ser and Cys residue, wherein the lateral chain is substituted by an aralkyl group, and
- $R^4$ represents the lateral chain of a natural amino acid or an analogue thereof.

4. Pseudo-peptide according to claim 1, wherein $R^3$ is an aralkyl group selected from the groups according to the formula:

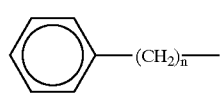
(II)

where n is an integer from 1 to 4, and according to the formula:

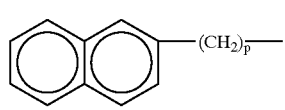
(III)

where p is equal to 1 or 2.

5. Pseudo-peptide according to claim 1 wherein $R^3$ is a group complying with any of the following formulas:

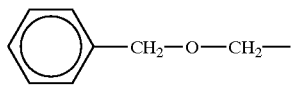
(IV)

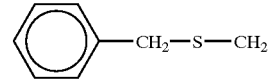
(V)

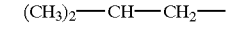
(VI)

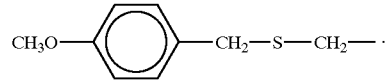
(VII)

6. Pseudo-peptide according to claim 1, wherein $R^3$ is the group according to the formula:

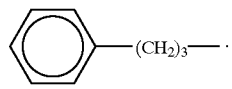
(VIII)

7. Pseudo-peptide according to claim 1 wherein $R^4$ represents the group according to the formula:

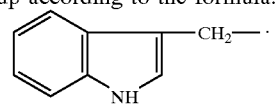

8. Pseudo-peptide according to claim 1, wherein $R^1$ represents a group selected from the group consisting of acetyl, benzyloxyacetyl, phenylaminoacetyl, (m-chlorophenyl)aminoacetyl, (2-hydroxy-5-chloro-phenyl) amino acetyl, indolyl-2-carbonyl, 4,6-dichloro-indolyl-2-carbonyl, quinolyl-2-carbonyl and 1-oxa-2,4-dichloro-7-naphthalene carbonyl groups.

9. Pseudo-peptide according to claim 1, which complies with the formula:

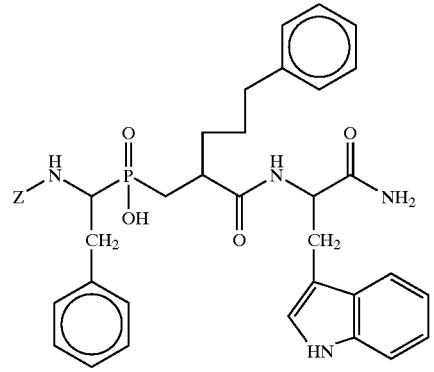

wherein Z is a benzyloxycarbonyl group.

10. Pseudo-peptide according to claim 9, wherein the unit

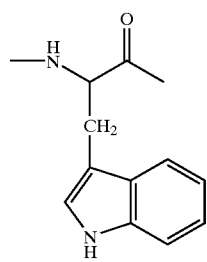

has an L configuration.

11. A method for inhibiting at least one matrix zinc metalloprotease in a subject in need thereof, comprising administering to said subject a pharmaceutical formulation comprising at least one pseudo-peptide according to claim 1.

12. Method according to claim 11, wherein the matrix zinc metalloprotease is selected from the group consisting of MMP-2, MMP-8, MMP-9 and MMP-11.

13. Method according to claim 11, wherein said inhibiting is for the treatment of a disease characterised by the overexpression of matrix proteases.

14. Method according to claim 13, wherein the disease is cancer.

15. Method according to claim 11, wherein the pseudo-peptide complies with the formula:

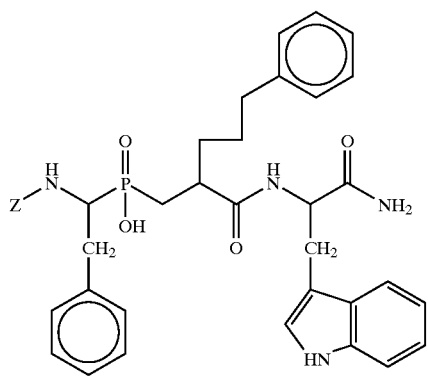

wherein Z is a benzyloxycarbonyl group.

16. Method according to claim 15, wherein the unit:

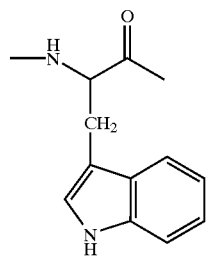

has an L configuration.

17. Pseudo-peptide according to claim 1, wherein $R^1$ represents a group selected from the group consisting of t-butoxycarbonyl, benzyloxycarbonyl, cinnamoyl, pivaloyl, and N-(1-fluorenyl-methoxycarbonyl) Fmoc groups.

18. Method according to claim 12, wherein said inhibiting is for the treatment of a disease characterised by the overexpression of matrix proteases.

19. Method according to claim 18, wherein the disease is cancer.

20. A pharmaceutical composition comprising at least one pseudo-peptide according to claim 1, in a therapeutically effective amount, and a pharmaceutically acceptable carrier.

21. Phosphinic pseudo-peptide according to claim 1, wherein $R^4$ represents a dinitrobenzyl group.

22. Phosphinic pseudo-peptide according to claim 2, wherein $R^4$ represents a dinitrobenzyl group.

* * * * *